(12) United States Patent
Baba-Ahmed et al.

(10) Patent No.: US 10,487,029 B2
(45) Date of Patent: Nov. 26, 2019

(54) AZEOTROPIC OR QUASI-AZEOTROPIC COMPOSITION COMPRISING TRIFLUOROPROPYNE

(71) Applicant: Arkema France, Colombes (FR)

(72) Inventors: Abdelatif Baba-Ahmed, Saint-fons (FR); Bertrand Collier, Saint-genis-laval (FR); Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/076,810

(22) PCT Filed: Mar. 3, 2017

(86) PCT No.: PCT/FR2017/050475
§ 371 (c)(1),
(2) Date: Aug. 9, 2018

(87) PCT Pub. No.: WO2017/149255
PCT Pub. Date: Sep. 8, 2017

(65) Prior Publication Data
US 2019/0016653 A1    Jan. 17, 2019

(30) Foreign Application Priority Data

Mar. 4, 2016 (FR) ..................... 16 51833

(51) Int. Cl.
*C07C 17/386* (2006.01)
*B01D 3/14* (2006.01)
*C07C 17/20* (2006.01)
*C07C 21/22* (2006.01)
*B01L 3/14* (2006.01)

(52) U.S. Cl.
CPC .............. *C07C 17/386* (2013.01); *B01L 3/14* (2013.01); *C07C 17/20* (2013.01); *C07C 21/22* (2013.01)

(58) Field of Classification Search
CPC ....... C07C 21/22; C07C 17/386; C07C 17/20; C07C 21/18; B01D 3/14
See application file for complete search history.

(56) References Cited

FOREIGN PATENT DOCUMENTS

WO    2013088195 A1    6/2013

OTHER PUBLICATIONS

EPO, International Search Report for International Application No. PCT/FR2017/050475 dated Jun. 21, 2017.

*Primary Examiner* — Jafar F Parsa
(74) *Attorney, Agent, or Firm* — NK Patent Law

(57) ABSTRACT

The invention relates to an azeotropic or quasi-azeotropic composition comprising hydrochloric acid and trifluoropropyne. The invention also relates to a method for separating 2,3,3,3-tetrafluoropropene and trifluoropropyne from a composition A containing 2,3,3,3-tetrafluoropropene and trifluoropropyne, said method comprising the steps of bringing said composition A into contact with an inorganic compound in order to form a composition B; and distilling composition B in order to from a first flow B1 containing trifluoropropyne and the inorganic compound, and a second flow B2 containing 2,3,3,3-tetrafluoropropene.

15 Claims, No Drawings

AZEOTROPIC OR QUASI-AZEOTROPIC COMPOSITION COMPRISING TRIFLUOROPROPYNE

This application is a U.S. National Stage application of International Application No. PCT/FR2017/050475 filed on Mar. 3, 2017, which claims the benefit of French Patent Application No. 1651833 filed on Mar. 4, 2016, the entire content of all of which is incorporated by reference herein.

TECHNICAL FIELD OF THE INVENTION

The present invention relates to an azeotropic composition comprising trifluoropropyne. The present invention also relates to a process for purifying a composition comprising trifluoropropyne and 2,3,3,3-tetrafluoropropene.

TECHNOLOGICAL BACKGROUND OF THE INVENTION

Fluorinated compounds such as hydrofluoroolefins are produced via fluorination or dehydrofluorination reactions of hydrofluorocarbons, hydrochlorocarbons or hydrochlorofluorocarbons. These reactions are generally carried out in the presence of hydrofluoric acid (HF) as fluorination agent. For example, WO2013/088195 describes the preparation of 2,3,3,3-tetrafluoropropene.

During these reactions, hydrochloric acid is produced. The latter may be separated from the other products of the reaction via a distillation column, in order ultimately to recover the hydrochloric acid without fluorinated impurities. Indeed, the hydrochloric acid recovered in gaseous form is subsequently absorbed in water in order to produce aqueous hydrochloric acid solutions which must have a low content of fluorinated products.

Aside from hydrochloric acid, light organic impurities may also be formed during fluorination reactions. Especially during the production of 2,3,3,3-tetrafluoropropene (1234yf), the light organic impurities are for example trifluoropropyne, trifluoromethane, pentafluoroethane, chloropentafluoroethane or 1,1,1-trifluoroethane. These light organic impurities are extracted from the desired product during purification thereof, via a distillation column intended for this purpose. The removal of these light organic impurities is generally accompanied by a loss of the desired product, the boiling point of which is often close to that of the light organic impurities. This may therefore reduce the overall yield of the process. Typically, the loss of the desired product due to the intermediate distillation of the light organic impurities is approximately 5%.

There is therefore still a need to employ a fluorination process that makes it possible to minimize losses of the desired product during the process for the purification thereof.

SUMMARY OF THE INVENTION

According to a first aspect of the present invention, an azeotropic or quasi-azeotropic composition comprising hydrochloric acid and trifluoropropyne is provided.

According to a particular embodiment, said azeotropic or quasi-azeotropic composition comprises from 85% by weight to 99.999% by weight of hydrochloric acid and from 0.001% by weight to 15% by weight of trifluoropropyne, based on the total weight of the composition; advantageously, said composition has a boiling point from 60° C. to 0° C.; preferably at a pressure of between 3 and 26 bara.

According to a preferred embodiment, said composition also comprises pentafluoroethane, chloropentafluoroethane or hexafluoroethane.

The applicant has established that employing the above azeotropic or quasi-azeotropic compositions facilitates the purification of 2,3,3,3-tetrafluoropropene, in particular promotes separation between 2,3,3,3-tetrafluoropropene and trifluoropropyne, which have relatively close boiling points.

According to a second aspect, the invention provides a process for separating 2,3,3,3-tetrafluoropropene and trifluoropropyne from a composition A comprising 2,3,3,3-tetrafluoropropene and trifluoropropyne, said process comprising the steps of:
 i) bringing said composition A into contact with an inorganic compound in order to form a composition B,
 ii) distilling the composition B in order to form a first stream B1 comprising trifluoropropyne and the inorganic compound; and a second stream B2 comprising 2,3,3,3-tetrafluoropropene.

According to a preferred embodiment, the trifluoropropyne and the inorganic compound form an azeotropic or quasi-azeotropic composition.

According to a preferred embodiment, the inorganic compound is hydrochloric acid.

According to a preferred embodiment, the amount of trifluoropropyne in said second stream B2 is less than the initial amount of trifluoropropyne in the composition B; advantageously, the amount of trifluoropropyne in the second stream B2 may be less than 10% of the initial amount of trifluoropropyne contained in the composition B; preferably, said second stream B2 comprises less than 1000 ppm of trifluoropropyne, more preferentially, said second stream B2 comprises less than 500 ppm of trifluoropropyne, in particular, said second stream B2 comprises less than 100 ppm, more particularly, said second stream B2 comprises less than 50 ppm; with particular preference, said second stream B2 is devoid of trifluoropropyne.

According to a third aspect, the invention provides a process for producing 2,3,3,3-tetrafluoropropene, comprising the steps of:
 A) fluorination in the presence of a catalyst for a compound of formula (I) $CX(Y)_2—CX(Y)_m—CH_mXY$ in which X and Y independently represent a hydrogen, fluorine or chlorine atom and m=0 or 1; and/or catalytic fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
 B) recovery of a stream C comprising 2,3,3,3-tetrafluoropropene, hydrochloric acid and trifluoropropyne;
 C) distilling the stream C recovered in step B) in order to form a first stream D comprising hydrochloric acid and trifluoropropyne; and a second stream E comprising 2,3,3,3-tetrafluoropropene.

According to a preferred embodiment, the first stream D comprising hydrochloric acid and trifluoropropyne is recovered at the top of the distillation column.

According to a preferred embodiment, the amount of trifluoropropyne in said second stream E is less than the initial amount of trifluoropropyne in the stream C; advantageously, the amount of trifluoropropyne in the second stream E may be less than 10% of the initial amount of trifluoropropyne contained in the stream C; preferably, said second stream E comprises less than 1000 ppm of trifluoropropyne, more preferentially, said second stream E comprises less than 500 ppm of trifluoropropyne, in particular, said second stream E comprises less than 100 ppm, more particularly, said second stream E comprises less than 50 ppm; with particular preference, said second stream E is devoid of trifluoropropyne.

According to a preferred embodiment, the first stream D comprises an azeotropic or quasi-azeotropic composition comprising from 85% by weight to 99.999% by weight of hydrochloric acid and from 0.001% by weight to 15% by weight of trifluoropropyne based on the total weight of the composition; advantageously, said composition has a boiling point from −60° C. to 0° C. preferably at a pressure of between 3 and 26 bara.

According to a preferred embodiment, the stream C recovered in step B) and the first stream D also comprise pentafluoroethane (F125), chloropentafluoroethane (F115) or hexafluoroethane (F116).

Preferably, the stream C recovered in step B) and the first stream D also comprise difluoromethane (32), 1,1,1-trifluoroethane (143a) and/or hydrofluoric acid.

According to a preferred embodiment, the stream C and the second stream E also comprise 1,1,1,2,2-pentafluoropropane, 1,3,3,3-tetrafluoropropene and impurities having a boiling point lower than the boiling point of 2,3,3,3-tetrafluoropropene; said second stream E being distilled in order to form a stream G comprising 2,3,3,3-tetrafluoropropene, 1,1,1,2,2-pentafluoropropane and 1,3,3,3-tetrafluoropropene; and a stream H comprising impurities having a boiling point lower than the boiling point of 2,3,3,3-tetrafluoropropene.

Employing an azeotropic or quasi-azeotropic composition of trifluoropropyne and hydrochloric acid makes it possible to readily purify 2,3,3,3-tetrafluoropropene from the trifluoropropyne and the hydrochloric acid produced during the fluorination reaction. The losses of 2,3,3,3-tetrafluoropropene are thereby minimized by removing, with the hydrochloric acid, at least trifluoropropyne which has a boiling point relatively close to that of 2,3,3,3-tetrafluoropropene.

DETAILED DESCRIPTION OF THE INVENTION

The invention is now described in greater detail and in a nonlimiting manner in the description which follows.

According to a first aspect, the invention provides an azeotropic or quasi-azeotropic composition comprising hydrochloric acid and trifluoropropyne.

The term "azeotropic composition" denotes a liquid mixture of two or more compounds which behave like a single substance, and which boils at a fixed temperature, maintaining a composition in the liquid phase that is identical to that in the gas phase. The term "quasi-azeotropic composition" denotes a liquid mixture of two or more compounds having a constant boiling point or which has a tendency not to fractionate when it is subjected to boiling or to evaporation.

According to a preferred embodiment, the composition comprises from 85% by weight to 99.999% by weight of hydrochloric acid and from 0.001% by weight to 15% by weight of trifluoropropyne based on the total weight of the composition. Advantageously, the composition comprises from 87% by weight to 99.999% by weight of hydrochloric acid and from 0.001% by weight to 13% by weight of trifluoropropyne based on the total weight of the composition. Preferably, the composition comprises from 88% by weight to 99.999% by weight of hydrochloric acid and from 0.001% by weight to 12% by weight of trifluoropropyne based on the total weight of the composition. In particular, the composition comprises from 90% by weight to 99.999% by weight of hydrochloric acid and from 0.001% by weight to 10% by weight of trifluoropropyne based on the total weight of the composition.

According to a preferred embodiment, said composition has a boiling point from −60° C. to 0° C., advantageously said composition has a boiling point from −55° C. to 0° C., preferably said composition has a boiling point from −50° C. to −5° C.

According to a preferred embodiment, said composition has a boiling point from −60° C. to 0° C., advantageously said composition has a boiling point from −55° C. to 0° C., preferably said composition has a boiling point from −50° C. to −5° C. at a pressure of 3 to 26 bara.

Advantageously, said composition has a boiling point from −60° C. to 0° C., advantageously said composition has a boiling point from −55° C. to 0° C., preferably said composition has a boiling point from −50° C. to −5° C. at a pressure of 4 to 26 bara.

Preferably, said composition has a boiling point from −60° C. to 0° C., advantageously said composition has a boiling point from −55° C. to 0° C., preferably said composition has a boiling point from −50° C. to −5° C. at a pressure of 5 to 23 bara.

According to a preferred embodiment, said composition also comprises pentafluoroethane (F125) and/or chloropentafluoroethane (F115) and/or hexafluoroethane (F116). Advantageously, the total proportion of pentafluoroethane (F125), of chloropentafluoroethane (F115) or of hexafluoroethane (F116) in said composition is less than 2% by weight based on the total weight of said composition. The total proportion relates to the sum of the individual proportions of pentafluoroethane (F125), chloropentafluoroethane (F115) and hexafluoroethane (F116). Preferably, the total proportion of pentafluoroethane (F125), chloropentafluoroethane (F115) or hexafluoroethane (F116) in said composition is less than 1% by weight based on the total weight of said composition, in particular less than 0.5% by weight, more particularly less than 0.1% by weight based on the total weight of said composition.

According to a second aspect, the present invention provides a process for separating 2,3,3,3-tetrafluoropropene and trifluoropropyne from a composition A comprising 2,3,3,3-tetrafluoropropene and trifluoropropyne, said process comprising the steps of:
i) bringing said composition A into contact with an inorganic compound in order to form a composition B,
ii) purifying, preferably distilling, the composition B in order to form a first stream B1 comprising trifluoropropyne and the inorganic compound; and a second stream B2 comprising 2,3,3,3-tetrafluoropropene.

The inorganic compound may be in liquid form or gaseous form. Preferably, the first stream B1 comprising trifluoropropyne and the inorganic compound forms an azeotropic or quasi-azeotropic composition. The first stream B1 may comprise from 85% to 99.999% by weight of inorganic compound and from 0.001% by weight to 15% by weight of trifluoropropyne based on the total weight of the first stream B1; advantageously from 87% by weight to 99.999% by weight of inorganic compound and from 0.001% to 13% by weight of trifluoropropyne; preferably from 88% by weight to 99.999% by weight of inorganic compound and from 0.001% by weight to 12% by weight of trifluoropropyne; in particular from 90% by weight to 99.999% by weight of inorganic compound and from 0.001% by weight to 10% by weight of trifluoropropyne.

According to a preferred embodiment, said inorganic compound is hydrochloric acid. Thus, the first stream B1 may comprise an azeotropic or quasi-azeotropic composition comprising trifluoropropyne and hydrochloric acid. The particularly preferred formation of the azeotropic or quasi-azeotropic composition comprising trifluoropropyne and hydrochloric acid facilitates the separation between the trifluoropropyne and 2,3,3,3-tetrafluoropropene contained in the composition A. Thus, the first stream B1 may therefore comprise, in azeotropic or quasi-azeotropic form, from 85% to 99.999% by weight of hydrochloric acid and from 0.001% by weight to 15% by weight of trifluoropropyne based on the total weight of the first stream B1; advantageously from 87% by weight to 99.999% by weight of hydrochloric acid and from 0.001% to 13% by weight of trifluoropropyne; preferably from 88% by weight to 99.999% by weight of hydrochloric acid and from 0.001% by weight to 12% by weight of trifluoropropyne; in particular, from 90% by weight to 99.999% by weight of hydrochloric acid and from 0.001% by weight to 10% by weight of trifluoropropyne.

The first stream B1 may have a boiling point from $-60°$ C. to $0°$ C., advantageously from $-55°$ C. to $0°$ C., preferably from $-50°$ C. to $-5°$ C. at a pressure of 3 to 26 bara. Advantageously, the first stream B1 may have a boiling point from $-60°$ C. to $0°$ C., advantageously from $-55°$ C. to $0°$ C., preferably from $-50°$ C. to $-5°$ C. at a pressure of 4 to 26 bara. Preferably, the first stream B1 may have a boiling point from $-60°$ C. to $0°$ C., advantageously said composition has a boiling point from $-55°$ C. to $0°$ C., preferably said composition has a boiling point from $-50°$ C. to $-5°$ C. at a pressure of 5 to 23 bara.

The second stream B2 comprising 2,3,3,3-tetrafluoropropene may contain a small amount of trifluoropropyne. The amount of trifluoropropyne in the second stream B2 is less than the initial amount of trifluoropropyne, expressed in mol, in the composition B. The amount of trifluoropropyne in the second stream B2 may be less than 50% of the initial amount of trifluoropropyne contained in the composition B. Advantageously, the amount of trifluoropropyne in the second stream B2 may be less than 25% of the initial amount of trifluoropropyne contained in the composition B. Preferably, the amount of trifluoropropyne in the second stream B2 may be less than 10% of the initial amount of trifluoropropyne contained in the composition B. In particular, the amount of trifluoropropyne in the second stream B2 may be less than 5% of the initial amount of trifluoropropyne contained in the composition B. More particularly, the amount of trifluoropropyne in the second stream B2 may be less than 1% of the initial amount of trifluoropropyne contained in the composition B.

According to a preferred embodiment, said second stream B2 comprises less than 1000 ppm of trifluoropropyne; advantageously, said second stream B2 comprises less than 500 ppm of trifluoropropyne; preferably, said second stream B2 comprises less than 100 ppm of trifluoropropyne; more preferentially, said second stream B2 comprises less than 50 ppm; in particular, said second stream B2 is devoid of trifluoropropyne. The term "devoid" as used here refers to an amount of trifluoropropyne in said second stream B2 less than 20 ppm, advantageously less than 10 ppm, preferably less than 1 ppm.

According to a third aspect, the invention provides a process for producing 2,3,3,3-tetrafluoropropene. Said process comprises the steps of:

A) fluorination in the presence of a catalyst for a compound of formula (I) $CX(Y)_2$—$CX(Y)_m$—$CH_mXY$ in which X and Y independently represent a hydrogen, fluorine or chlorine atom and m=0 or 1; and/or fluorination in the presence of a catalyst for a compound of formula $(CX_nY_{3-n})CH_pX_{1-p}CH_mX_2$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream C comprising 2,3,3,3-tetrafluoropropene, hydrochloric acid and trifluoropropyne;

C) purifying, preferably distilling, the stream C recovered in step B) in order to form a first stream D comprising hydrochloric acid and trifluoropropyne; and a second stream E comprising 2,3,3,3-tetrafluoropropene.

According to a preferred embodiment, step A) of the present process may be carried out in the presence of a catalyst from a compound of formula (I) or (II) selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za), 3,3,3-trichloropropene (HCO-1240zf). Preferably, step A) of the present process may be carried out in the presence of a catalyst from a compound of formula (I) or (II) selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb).

Preferably, the catalytic fluorination is carried out in the gas phase.

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example approximately 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF. For example, the catalyst is preferably subjected to activation with air or oxygen and HF at a temperature from 100 to 500° C., preferably from 250 to 500° C. and more particularly from 300 to 400° C. The duration of activation is preferably from 1 to 200 h and more particularly from 1 to 50 h. This activation may be followed by a final fluorination activation step in the presence of an oxidizing agent, HF and organic compounds. The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
  with an HF/compound of formula (I) and/or (II) mole ratio from 3:1 to 150:1, preferably from 4:1 to 125:1 and more particularly preferably from 5:1 to 100:1;
  with a contact time from 3 to 100 seconds, preferably 4 to 75 seconds and more particularly 5 to 50 seconds (volume of catalyst divided by the total entering stream, adjusted to the operating temperature and pressure);
  at a pressure ranging from atmospheric pressure to 20 bar, preferably from 2 to 18 bar and more particularly from 3 to 15 bar;
  at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

Preferably, the first stream D comprising hydrochloric acid and trifluoropropyne is recovered at the top of the distillation column. Preferably, the first stream D is an azeotropic or quasi-azeotropic composition of hydrochloric acid and trifluoropropyne.

The formation of an azeotropic or quasi-azeotropic composition of hydrochloric acid and trifluoropropyne makes it possible to improve the separation between the trifluoropropyne and 2,3,3,3-tetrafluoropropene. Thus, the stream E comprising 2,3,3,3-tetrafluoropropene will be devoid of trifluoropropyne or will contain sufficiently small amounts thereof in order to facilitate the subsequent purification thereof.

According to a preferred embodiment, the first stream D may comprise, in azeotropic or quasi-azeotropic form, from 85% to 99.999% by weight of hydrochloric acid and from 0.001% by weight to 15% by weight of trifluoropropyne based on the total weight of the first stream D; advantageously from 87% by weight to 99.999% by weight of hydrochloric acid and from 0.001% to 13% by weight of trifluoropropyne; preferably from 88% by weight to 99.999% by weight of hydrochloric acid and from 0.001% by weight to 12% by weight of trifluoropropyne; in particular, from 90% by weight to 99.999% by weight of hydrochloric acid and from 0.001% by weight to 10% by weight of trifluoropropyne.

The first stream D may have a boiling point from −60° C. to 0° C., advantageously from −55° C. to 0° C., preferably from −50° C. to −5° C. at a pressure of 3 to 26 bara. Advantageously, the first stream D may have a boiling point from −60° C. to 0° C., advantageously from −55° C. to 0° C., preferably from −50° C. to −5° C. at a pressure of 4 to 26 bara. Preferably, the first stream D may have a boiling point from −60° C. to 0° C., advantageously from −55° C. to 0° C., preferably from −50° C. to −5° C. at a pressure of 5 to 23 bara.

Preferably, step C) of the present process is carried out under operating conditions suitable for enabling the formation of the first stream D comprising hydrochloric acid and one or more compounds forming azeotropes or quasi-azeotropes with hydrochloric acid. Aside from the HCl/trifluoropropyne azeotrope or quasi-azeotrope, step C) may be carried out so as to recover, in said first stream D, the HCl/pentafluoroethane (F125), HCl/chloropentafluoroethane (F115) and/or HCl/hexafluoroethane (F116) azeotrope or quasi-azeotrope. Thus, aside from trifluoropropyne, other light organic impurities may be recovered with the hydrochloric acid. Thus, the distillation intended to eliminate light organic impurities may be dispensed with or at least facilitates so as to minimize losses of 2,3,3,3-tetrafluoropropene.

Thus, according to a particular embodiment, the stream C recovered in step B) and said first stream D also comprise pentafluoroethane (F125) and/or chloropentafluoroethane (F115) and/or hexafluoroethane (F116). Advantageously, the total proportion of pentafluoroethane (F125), of chloropentafluoroethane (F115) or of hexafluoroethane (F116) in said first stream D is less than 2% by weight based on the total weight of said composition. Preferably, the total proportion of pentafluoroethane (F125), chloropentafluoroethane (F115) or hexafluoroethane (F116) in said first stream D is less than 1% by weight based on the total weight of said first stream D, in particular less than 0.5% by weight, more particularly less than 0.1% by weight.

According to a particular embodiment, the stream C recovered in step B) and the first stream D also comprise difluoromethane (F32) and/or 1,1,1-trifluoroethane (F143a) and/or hydrofluoric acid. Advantageously, the total proportion of difluoromethane and/or of 1,1,1-trifluoroethane and/or of hydrofluoric acid is less than 0.5% by weight based on the total weight of the first stream D.

According to a particular embodiment, the first stream D may be purified to form a composition comprising hydrochloric acid in which the content of trifluoropropyne is less than 20 ppm, advantageously less than 10 ppm, preferably less than 1 ppm. Said first stream D may be purified by carrying out a step of catalytic hydrolysis; washing with an acid solution, and/or one or more steps of adsorption of impurities by an adsorbent.

Preferably, the step of catalytic hydrolysis may be carried out by bringing said first stream D into contact with a catalytic bed, which is preferably a bed of activated carbon, in the presence of water. The temperature of the catalytic hydrolysis step is preferably from 100 to 200° C., especially from 120 to 170° C., and more particularly from 130 to 150° C. The pressure is preferably from 0.5 to 3 barg, especially from 1 to 2 barg. The contact time is preferably from 1 s to 1 min, especially from 2 s to 30 s, more particularly from 4 s to 15 s, and most particularly from 5 s to 10 s. The amount of water is said first stream D subjected to the catalytic hydrolysis is adjusted such that the mole ratio of water relative to the sum of the compounds other than hydrochloric acid in said first stream D is greater than 1, preferably greater than or equal to 2, or to 3, or to 4, or to 5, or to 6, or to 6.5. A supply of water may be provided, if necessary. The step of catalytic hydrolysis may be carried out in order to hydrolyze compounds such as $COF_2$, COFCl, $CF_3COF$, if they are present in the stream C and the first stream D. Following this step of catalytic hydrolysis, a stream F1 is recovered. This stream F1 comprises, aside from hydrochloric acid, trifluoropropyne and optionally pentafluoroethane (F125), chloropentafluoroethane (F115), hexafluoroethane (F116), difluoromethane (F32), 1,1,1-trifluoroethane (F143a) and/or hydrofluoric acid and optionally trifluoroacetic acid resulting from the hydrolysis of $CF_3COF$. The step of washing with an acid solution may be carried out in a plate column, such as a perforated plate column, or a bubble cap column, or a valve plate column or a column of Dualflow® type. It may also be a packed column. The gas stream F1 is preferably washed countercurrentwise: the gas stream F1 is fed at the bottom and an acid solution is fed at the top of the column. Use may especially be made, as acid solution, of an HCl solution at a concentration by weight which may range, for example, from 5 to 60%, especially from 10 to 50%, more preferentially from 20 to 45% and in particular from 30 to 35%. The washing by the acid solution is preferably carried out at a temperature of 5 to 50° C. and more particularly from 7 to 40° C.; and/or at a pressure of 0.1 to 4 barg, preferably of 0.3 to 2 barg, more preferentially from 0.5 to 1.5 barg. Addition of boric acid at the stage of washing with the acid solution may also be carried out in order to complex the fluoride ions. For example, the addition of 2000 to 8000 ppm of $H_3BO_3$ makes it possible to improve the elimination of certain fluorinated compounds. The washed gas stream F2 resulting from the washing step may be subjected to a step of adsorption on an activated carbon bed in order to form a stream F3. The impurities adsorbed by the activated carbon bed are primarily trifluoropropyne and optionally pentafluoroethane (F125), chloropentafluoroethane (F115), hexafluoroethane (F116), difluoromethane (F32) or 1,1,1-trifluoroethane (F143a). The step of adsorption on activated carbon bed may be carried out in pressure and temperature ranges which have already been indicated above in relation to the step of washing with an acid solution. The purified gas stream F3 is subjected to a step of adiabatic or isothermal absorption, making it possible to absorb the hydrochloric acid from the gas stream F3 in an aqueous solution in order to form an aqueous solution of hydrochloric acid F4. This aqueous solution may simply be demineralized water, or alternatively may be an acid solution. Generally, this absorption step is carried out on a column for bringing into contact countercurrentwise, the aqueous solution being provided at the top and the gas stream at the bottom. Since the reaction for absorption of the hydrochloric acid in the water is exothermic, it is preferable to limit the pressure at which this operation is carried out. In general, the pressure is less than 2 barg and preferably less than 1.5 barg. In this way, the absorption temperature does not exceed 130° C., and preferably 120° C. In order to withstand corrosion, the column may be made of graphite or else of steel coated with polytetrafluoroethylene (PTFE). The column internals may, for example, be either made of graphite or of polyvinylidene fluoride (PVDF). A deacidified gas stream F5 is collected at the top. This stream may either be discharged to the atmosphere via a neutralization safety column or sent to an incinerator. A solution of hydrochloric acid F4 is collected at the bottom. The concentration by weight of hydrochloric acid in the solution F4 may be from 5 to 50%, preferably from 15 to 40%, and more particularly from 30 to 35%. If the purity of the collected solution of hydrochloric acid F4 is insufficient, and especially if the content of HF remains above the desired threshold, it is possible to carry out another treatment step, namely a step of adsorption on a silica gel. The temperature of the solution of hydrochloric acid F4 must be as low as possible, and for example less than or equal to 35° C., since adsorption on silica gel is exothermic. Above this temperature, the adsorption effectiveness decreases greatly. The contact time is between a few minutes and a few hours (preferably between 10 and 60 min). The rates of passage are slow and between 1 and 20 m/h and preferably between 3 and 10 m/h. The operating pressure is a few bar (from 1 to 7 barg and preferably from 1 to 5 barg). The silica gel typically comprises a pore size of 50 Å, whereas conventional gels generally have pore sizes of 20 Å at most. The fluoride content of the HCl solution at the inlet is preferably less than or equal to 100 ppm in order to avoid any risk of damage to the silica gel.

According to a preferred embodiment, the second stream E recovered in step C) of the present process comprising 2,3,3,3-tetrafluoropropene may contain a small amount of trifluoropropyne. Preferably, the amount of trifluoropropyne in the second stream E may be less than 10% of the initial amount of trifluoropropyne contained in the stream C. In particular, the amount of trifluoropropyne in the second stream E may be less than 5% of the initial amount of trifluoropropyne contained in the stream C. More particularly, the amount of trifluoropropyne in the second stream E may be less than 1% of the initial amount of trifluoropropyne contained in the stream C.

According to a preferred embodiment, said second stream E comprises less than 1000 ppm of trifluoropropyne; advantageously, said second stream E comprises less than 500 ppm of trifluoropropyne; preferably, said second stream E comprises less than 100 ppm of trifluoropropyne; in particular, said second stream E is devoid of trifluoropropyne. The term "devoid" as used here refers to an amount of trifluoropropyne in said second stream E less than 20 ppm, advantageously less than 10 ppm, preferably less than 1 ppm.

According to a preferred embodiment, the stream C and the second stream E also comprise 1,1,1,2,2-pentafluoropropane (245cb), 1,3,3,3-tetrafluoropropene (1234ze) and impurities having a boiling point lower than the boiling point of 2,3,3,3-tetrafluoropropene; said second stream E being distilled in order to form a stream G comprising 2,3,3,3-tetrafluoropropene (1234yf), 1,1,1,2,2-pentafluoropropane (245cb) and 1,3,3,3-tetrafluoropropene (1234ze); and a stream H comprising impurities having a boiling point lower than the boiling point of 2,3,3,3-tetrafluoropropene. The impurities having a boiling point lower than the boiling point of 2,3,3,3-tetrafluoropropene may be trifluoromethane (F23) and/or monofluoromethane (F41). In addition, the second stream E may comprise difluoromethane (F32), pentafluoroethane (F125), 1,1,1-trifluoroethane (F143a), trifluoropropyne or 1-chloropentafluoroethane (F115) in very small amounts. Thus, the second stream E comprises less than 10 ppm of difluoromethane (F32), less than 10 ppm of pentafluoroethane (F125), less than 10 ppm of 1,1,1-trifluoroethane (F143a), less than 10 ppm of trifluoropropyne and/or less than 10 ppm of 1-chloropentafluoroethane (F115).

According to a preferred embodiment, the stream G comprising 2,3,3,3-tetrafluoropropene, 1,1,1,2,2-pentafluoropropane and 1,3,3,3-tetrafluoropropene contains less than 1 ppm of difluoromethane (F32), less than 1 ppm of pentafluoroethane (F125), less than 1 ppm of 1,1,1-trifluoroethane (F143a), less than 1 ppm of trifluoropropyne and/or less than 1 ppm of 1-chloropentafluoroethane (F115), if the second stream E contained one of these compounds.

The applicant has thus demonstrated that the combined elimination of hydrochloric acid and of trifluoropropyne makes it possible to minimize the losses of 2,3,3,3-tetrafluoropropene by dispensing with, or facilitating, the distillation intended for the elimination of light organic impurities, given the low contents of light organic impurities contained in the second stream E.

EXAMPLE

Formation of the hydrochloric acid/trifluoropropyne azeotrope or quasi-azeotrope was simulated with the Aspen software. The results are presented in table 1 below:

Table 1

| HCl-Trifluoropropyne azeotrope | | | |
|---|---|---|---|
| Temperature | Pressure | Azeotropic composition | |
| °C. | bara | % by weight HCl | % by weight trifluoropropyne |
| −60 | 3.72 | 93 | 7 |
| −55 | 4.33 | 94 | 6 |
| −50 | 5.29 | 95 | 5 |
| −45 | 6.4 | 97 | 3 |
| −42 | 7.15 | 97.5 | 2.5 |
| −41 | 7.41 | 97.5 | 2.5 |
| −40 | 7.69 | 98.5 | 1.5 |
| −39 | 7.96 | 98.5 | 1.5 |
| −38 | 8.25 | 99 | 1 |
| −37 | 8.54 | 99 | 1 |

The invention claimed is:

1. An azeotropic or quasi-azeotropic composition comprising hydrochloric acid and trifluoropropyne, wherein the composition comprising from 85% by weight to 99.999% by weight of hydrochloric acid and from 0.001% by weight to 15% by weight of trifluoropropyne, based on the total weight of the composition; wherein, said composition has a boiling point from −60° C. to 0° C.

2. The composition of claim 1, further comprising pentafluoroethane, chloropentafluoroethane or hexafluoroethane.

3. A process for separating 2,3,3,3-tetrafluoropropene and trifluoropropyne from a composition A comprising 2,3,3,3-tetrafluoropropene and trifluoropropyne, said process comprising:

i) bringing said composition A into contact with an inorganic compound in order to form a composition B;
ii) distilling the composition B in order to form a first stream B1 comprising trifluoropropyne and the inorganic compound; and a second stream B2 comprising 2,3,3,3-tetrafluoropropene;
wherein said inorganic compound comprises hydrochloric acid, wherein said first stream B1 and the inorganic compound form an azeotropic or quasi-azeotropic composition.

4. The process of claim 3, wherein said second stream B2 further comprises trifluoropropyne and wherein the amount of trifluoropropyne of said second stream B2 is less than the initial amount of trifluoropropyne in the composition B.

5. The process of claim 4, wherein the amount of trifluoropropyne in the second stream B2 is less than 10% of the initial amount of trifluoropropyne contained in the composition B.

6. The process of claim 5, wherein said second stream B2 comprises less than 1000 ppm of trifluoropropyne.

7. A process for producing 2,3,3,3-tetrafluoropropene, comprising:

A. fluorination in the presence of a catalyst for a compound of formula (I) $CX(Y)_2—CX(Y)_m—CH_mXY$ in which X and Y independently represent a hydrogen, fluorine or chlorine atom and m=0 or 1; and/or fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
B. recovering a stream C comprising 2,3,3,3-tetrafluoropropene, hydrochloric acid and trifluoropropyne; and
C. distilling stream C recovered in step B) in order to form a first stream D comprising hydrochloric acid and trifluoropropyne form an azeotropic or quasi-azeotropic composition; and a second stream E comprising 2,3,3,3-tetrafluoropropene.

8. The process of claim 7, wherein the first stream D comprising hydrochloric acid and trifluoropropyne is recovered at the top of the distillation column.

9. The process of claim 7, wherein said second stream E further comprises trifluoropropyne and wherein the amount of trifluoropropyne in said second stream E is less than the initial amount of trifluoropropyne in stream C.

10. The process of claim 9, wherein the amount of trifluoropropyne in the second stream E is less than 10% of the initial amount of trifluoropropyne contained in stream C.

11. The process of claim 10, wherein said second stream E comprises less than 1000 ppm of trifluoropropyne.

12. The process of claim 7, wherein the first stream D comprises an azeotropic or quasi-azeotropic composition comprising from 85% by weight to 99.999% by weight of hydrochloric acid and from 0.001% by weight to 15% by weight of trifluoropropyne based on the total weight of the first stream D; wherein, said composition has a boiling point from −60° C. to 0° C.

13. The process of claim 7, wherein the stream C and the first stream D further comprise pentafluoroethane (F125), chloropentafluoroethane (F115), hexafluoroethane (F116), or mixtures thereof.

14. The process of claim 7, wherein the stream C and the first stream D further comprise difluoromethane (32), 1,1,1-trifluoroethane (143a), hydrofluoric acid, or mixtures thereof.

15. The process of claim 7, wherein the stream C and the second stream E further comprise 1,1,1,2,2-pentafluoropropane, 1,3,3,3-tetrafluoropropene and impurities having a boiling point lower than the boiling point of 2,3,3,3-tetrafluoropropene; and the process further comprises distilling said second stream E in order to form a stream G comprising 2,3,3,3-tetrafluoropropene, 1,1,1,2,2-pentafluoropropane and 1,3,3,3-tetrafluoropropene; and a stream H comprising impurities having a boiling point lower than the boiling point of 2,3,3,3-tetrafluoropropene.

* * * * *